US011827935B1

(12) United States Patent
Ramachandran Iyer et al.

(10) Patent No.: US 11,827,935 B1
(45) Date of Patent: Nov. 28, 2023

(54) METHODS FOR SPATIAL ANALYSIS USING ROLLING CIRCLE AMPLIFICATION AND DETECTION PROBES

(71) Applicant: 10x Genomics, Inc., Pleasanton, CA (US)

(72) Inventors: Eswar Prasad Ramachandran Iyer, Pleasanton, CA (US); Yifeng Yin, Elk Grove, CA (US); Sultan Doganay Tuncer, Pleasanton, CA (US)

(73) Assignee: 10x Genomics, Inc., Pleasanton, CA (US)

(*) Notice: Subject to any disclaimer, the term of this patent is extended or adjusted under 35 U.S.C. 154(b) by 0 days.

(21) Appl. No.: 17/531,093

(22) Filed: Nov. 19, 2021

Related U.S. Application Data

(60) Provisional application No. 63/115,916, filed on Nov. 19, 2020.

(51) Int. Cl.
*C12Q 1/6874* (2018.01)
*C12Q 1/6855* (2018.01)
*C12Q 1/6862* (2018.01)

(52) U.S. Cl.
CPC ......... *C12Q 1/6874* (2013.01); *C12Q 1/6855* (2013.01); *C12Q 1/6862* (2013.01)

(58) Field of Classification Search
CPC .. C12Q 1/6874; C12Q 1/6855; C12Q 1/6862; C12Q 2563/179; C12Q 2531/125; C12Q 2525/307; C12Q 2565/501
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 4,988,617 A | 1/1991 | Landegren et al. | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,641,658 A | 6/1997 | Adams | |
| 5,648,245 A | 7/1997 | Fire et al. | |
| 5,658,751 A | 8/1997 | Yue | |
| 5,695,940 A | 12/1997 | Drmanac et al. | |
| 5,750,341 A | 5/1998 | Macevicz | |
| 5,763,175 A | 6/1998 | Brenner | |
| 5,830,711 A | 11/1998 | Barany et al. | |
| 5,837,832 A | 11/1998 | Chee et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 5,925,545 A | 7/1999 | Reznikoff et al. | |
| 5,928,906 A | 7/1999 | Koester et al. | |
| 5,958,775 A | 9/1999 | Wickstrrom | |
| 5,965,443 A | 10/1999 | Reznikoff et al. | |
| 6,013,440 A | 1/2000 | Lipshutz | |
| 6,027,889 A | 2/2000 | Barany et al. | |
| 6,054,274 A | 4/2000 | Sampson et al. | |
| 6,060,240 A | 5/2000 | Kamb et al. | |
| 6,130,073 A | 10/2000 | Eggerding | |
| 6,143,496 A | 11/2000 | Brown | |
| 6,153,389 A | 11/2000 | Haarer | |
| 6,159,736 A | 12/2000 | Reznikoff et al. | |
| 6,165,714 A | 12/2000 | Lane et al. | |
| 6,210,891 B1 | 4/2001 | Nyren | |
| 6,210,894 B1 | 4/2001 | Brennan | |
| 6,214,587 B1 | 4/2001 | Dattagupta | |
| 6,251,639 B1 | 6/2001 | Kurn | |
| 6,258,568 B1 | 7/2001 | Nyren | |
| 6,266,459 B1 | 7/2001 | Walt | |
| 6,268,148 B1 | 7/2001 | Barany et al. | |
| 6,274,320 B1 | 8/2001 | Rothberg | |
| 6,291,180 B1 | 9/2001 | Chu | |
| 6,291,187 B1 | 9/2001 | Kingsmore et al. | |
| 6,300,063 B1 | 10/2001 | Lipshutz et al. | |
| 6,309,824 B1 | 10/2001 | Drmanac | |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Marx, "Method of the Year: spatially resolved transcriptomics," Nature Methods, 2021, 18(1):9-14.

(Continued)

*Primary Examiner* — David C Thomas
(74) *Attorney, Agent, or Firm* — Fish & Richardson P.C.

(57) ABSTRACT

Provided herein are methods of improving sensitivity of spatial detection of an analyte in a biological sample using splint oligonucleotides, circularized second strands, and rolling circle amplification. For example, provided herein are methods of improving sensitivity of spatial detection of an analyte in a biological sample where a splint oligonucleotide hybridizes to a second strand; the second strand is ligated together thereby creating a circularized second strand, rolling circle amplification of the circularized second strand results in generation of an amplified second strand, and all or part of the sequence of the amplified second strand is determined and used to spatially detect the analyte in the biological sample.

20 Claims, 5 Drawing Sheets

(56) References Cited

U.S. PATENT DOCUMENTS

| | | |
|---|---|---|
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |

(56) References Cited

U.S. PATENT DOCUMENTS

| | | |
|---|---|---|
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier et al. |
| 11,530,438 B2 * | 12/2022 | Persson ................ C12Q 1/6851 |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |

(56) References Cited

U.S. PATENT DOCUMENTS

| | | |
|---|---|---|
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0065768 A1 | 3/2013 | Zheng et al. |
| 2013/0079232 A1 | 3/2013 | Kain et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |

(56) References Cited

U.S. PATENT DOCUMENTS

| | | |
|---|---|---|
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0055594 A1 | 2/2019 | Samusik et al. |
| 2019/0064173 A1 | 2/2019 | Bharadwaj et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |

(56) References Cited

U.S. PATENT DOCUMENTS

| | | |
|---|---|---|
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/093098 | 8/2008 |
| WO | WO 2009/032167 | 3/2009 |
| WO | WO 2009/036525 | 3/2009 |

(56) References Cited

FOREIGN PATENT DOCUMENTS

| | | |
|---|---|---|
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047010 | 3/2020 |
| WO | WO 2020/053655 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |

(56) References Cited

FOREIGN PATENT DOCUMENTS

| WO | WO 2023/150098 | 8/2023 |
|---|---|---|
| WO | WO 2023/150163 | 8/2023 |
| WO | WO 2023/150171 | 8/2023 |

OTHER PUBLICATIONS

Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
U.S. Appl. No. 16/353,937, filed Mar. 14, 2019, Frisen et al.
U.S. Appl. No. 17/707,189, filed Mar. 29, 2022, Chell et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, p. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.

(56) References Cited

OTHER PUBLICATIONS

Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.

(56) References Cited

OTHER PUBLICATIONS

Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
FLUIDIGM, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.

(56) References Cited

OTHER PUBLICATIONS

He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," Embo J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.

(56) References Cited

OTHER PUBLICATIONS

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lin et al., "Highly multiplexed imaging of single cells using a high-throughput cyclic immunofluorescence method," Nat Commun., Sep. 2015, 6:8390, 7 pages.

Linnarsson, "Recent advances in DNA sequencing methods—general principles of sample preparation," Experimental Cell Research, 2010, 316(8):1339-1343.

Liu et al., "High-Spatial-Resolution Multi-Omics Atlas Sequencing of Mouse Embryos via Deterministic Barcoding in Tissue," BioRxiv, 2019, 55 pages.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

Lizardi et al., "Mutation detection and single-molecule counting using isothermal rolling-circle amplification," Nat. Genet., 1998, 19(3):225-232.

Lou et al., "A review of room temperature storage of biospecimen tissue and nucleic acids for anatomic pathology laboratories and biorepositories," Clin Biochem., Mar. 2014, 47(4-5):267-73.

Lovatt et al., "Transcriptome in vivo analysis (TIVA) of spatially defined single cells in live tissue," Nature Methods, 2013, 11(2):190-196.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.

Lundin et al., "Increased throughput by parallelization of library preparation for massive sequencing," PLoS One, Apr. 2010, 5(4):e10029, 7 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Lyck et al., "Immunohistochemical markers for quantitative studies of neurons and glia in human neocortex," J Histochem Cytochem, 2008, 56(3):201-21.

Lykidis et al., "Novel zinc-based fixative for high quality DNA, RNA and protein analysis," Nucleic Acids Res., Jun. 2007, 35(12):e85, 10 pages.

Ma et al., "Isothermal amplification method for next-generation sequencing," PNAS, Aug. 12, 2013, 110(35):14320-14323.

MacBeath et al., "Printing proteins as microarrays for high-throughput function determination," Science, Sep. 2000, 289(5485):1760-1763.

MacIntyre, "Unmasking antigens for immunohistochemistry.," Br J Biomed Sci., 2001, 58(3):190-6.

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miele et al., "Mapping cis- and trans-chromatin interaction networks using chromosome conformation capture (3C)," Methods Mol Biol., 2009, 464:105-21.

Mignardi et al., "Oligonucleotide gap-fill ligation for mutation detection and sequencing in situ," Nucleic Acids Research, Aug. 3, 2015, 43(22):e151, 12 pages.

Miller et al., "Basic concepts of microarrays and potential applications in clinical microbiology," Clinical Microbiology Reviews, 2009, 22(4):611-633.

Miller et al., "Chapter 11—Solid and Suspension Microarrays for Microbial Diagnostics," Methods in Microbiology, 2015, 42:395-431.

Miner et al., "Molecular barcodes detect redundancy and contamination in hairpin-bisulfite PCR," Nucleic Acids Res., Sep. 2004, 32(17):e135, 4 pages.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.

Mizusawa et al., "A bacteriophage lambda vector for cloning with BamHI and Sau3A," Gene, 1982, 20(3):317-322.

Mohsen et al., "The Discovery of Rolling Circle Amplification and Rolling Circle Transcription," Acc Chem Res., Nov. 15, 2016, 49(11):2540-2550, 25 pages.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Mulder et al., "CapTCR-seq: hybrid capture for T-cell receptor repertoire profiling," Blood Advances, Dec. 2018, 2(23):3506-3514.

Nadji et al., "Immunohistochemistry of tissue prepared by a molecular-friendly fixation and processing system," Appl Immunohistochem Mol Morphol., Sep. 2005, 13(3):277-82.

Nallur et al., "Signal amplification by rolling circle amplification on DNA microarrays," Nucleic Acids Res., Dec. 1, 2001, 29(23):e118, 9 pages.

Nandakumar et al., "How an RNA Ligase Discriminates RNA versus DNA Damage," Molecular Cell, 2004, 16:211-221.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niedringhaus et al., "Landscape of next-generation sequencing technologies," Anal Chem., Jun. 2011, 83(12):4327-41.

(56) References Cited

OTHER PUBLICATIONS

Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Orenstein et al., "γPNA FRET Pair Miniprobes for Quantitative Fluorescent in Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc 1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.

(56) References Cited

OTHER PUBLICATIONS

Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Takei et al., "Integrated Spatial Genomics Reveals Global Architecture of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS One, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.

Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.

(56) References Cited

OTHER PUBLICATIONS

Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin a expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Bibikova et al., "Quantitative gene expression profiling in formalin-fixed paraffin-embedded tissues using universal bead arrays," The American Journal of Pathology, Nov. 1, 2004, 165(5):1799-1807.
Chen et al. "Arrayed profiling of multiple glycans on whole living cell surfaces." Analytical chemistry, Oct. 15, 2013, 85(22):11153-11158.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Hobro et al, "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Schmidl et al., "ChIPmentation: fast, robust, low-input ChIP-seq for histones and transcription factors," Nature Methods, Oct. 2015, 12:963-965.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Su et al., "Restriction enzyme selection dictates detection range sensitivity in chromatin conformation capture-based variant-to-gene mapping approaches," bioRxiv, Dec. 15, 2020, 22 pages.

* cited by examiner

METHODS FOR SPATIAL ANALYSIS USING ROLLING CIRCLE AMPLIFICATION AND DETECTION PROBES

CROSS-REFERENCE TO RELATED APPLICATIONS

This application claims the benefit of U.S. Provisional Application Ser. No. 63/115,916, filed Nov. 19, 2020, the entire contents of which are incorporated by reference herein.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provides substantial analyte data for dissociated tissue (i.e., single cells), but fail to provide information regarding the position of the single cell in a parent biological sample (e.g., tissue sample).

Generally, spatial analysis requires determining the sequence of the analyte sequence or a complement thereof and the sequence of the spatial barcode or a complement thereof in order to identify spatial location of the analyte. Typically, this requires sequencing which can be time and resource intensive. Therefore, there is a need to assess analyte and biological sample quality prior to spatial analysis.

SUMMARY

Spatial analysis requires processing of a captured analyte in order to determine its abundance and location in a biological sample. During this process, after capture of the analyte, a process of second strand synthesis is performed. This process includes generating a single-stranded nucleic acid that is complementary both to the capture probe and to the analyte (or a complement thereof). After, the second strand can be further processed, placed in a library, and sequenced. The disclosure has identified that sensitivity can be lost during second strand synthesis. To address this issue, the disclosure provides methods of generating an amplified product comprising the capture probe or complement thereof and analyte or complement thereof using a splint oligonucleotide and rolling circle amplification—all performed on a substrate.

In one embodiment, disclosed herein is a method of determining location and abundance of an analyte in a biological sample. In some instances, the method includes: (a) hybridizing the analyte to a capture probe on an array, wherein the capture probe comprises a spatial barcode and a capture domain; (b) extending the capture probe using the analyte as a template, thereby generating an extended capture probe, and generating a second strand comprising a sequence that is complementary to (i) the analyte or a complement thereof and (ii) the spatial barcode or a complement thereof; (c) denaturing the second strand from the extended capture probe under conditions wherein a 5' end of the second strand and a 3' end of the second strand dehybridize from the extended capture probe; (d) hybridizing a splint oligonucleotide both to the 5' end of the second strand and to the 3' end of the second strand; (e) generating a circularized second strand; (f) amplifying the circularized second strand, thereby creating an amplified second strand; and (g) determining all or part of the sequence of the amplified second strand to determining the location and the abundance of the analyte in the biological sample.

In some instances, the analyte comprises a capture domain capture sequence that hybridizes to the capture domain, and wherein the capture domain comprises a poly (T) sequence. In some instances, the capture domain capture sequence comprises a poly(A) sequence. In some instances, the array comprises a plurality of capture probes.

In some instances, extending the capture probe and generating a second strand utilize a polymerase or reverse transcriptase. In some instances, denaturing comprises increasing the temperature, thereby dehybridizing the 5' end of the second strand and the 3' end of the second strand from the extended capture probe. In some instances, before step (e) above, the method includes extending the 5' end of the second strand using the splint oligonucleotide as a template, thereby creating an extended 5' end. In some instances, generating the circularized second strand comprises ligating the extended second portion to the first portion using a ligase. In some instances, the ligase is a T4 DNA ligase.

In some instances, amplifying the circularized second strand comprises rolling circle amplification (RCA) using the circularized second strand as a template. In some instances, the amplified second strand comprises (i) the spatial barcode or complement thereof and (ii) all or part of the analyte or a complement thereof. In some instances, the method further includes hybridizing an oligonucleotide to a portion of the amplified second strand, thereby producing a double-stranded sequence, and wherein the double-stranded sequence comprises a restriction site. In some instances, the method further includes digesting the double-stranded sequence using a restriction enzyme.

In some instances, the splint oligonucleotide comprises a first sequence that is substantially complementary to the 5' end of the second strand, and a second sequence that is substantially complementary to the 3' end of the second strand. In some instances, the capture probe further comprises one or more functional domains, a unique molecular identifier, a cleavage domain, and combinations thereof. In some instances, the method further includes phosphorylating the 5' end of the splint oligonucleotide prior to the ligation step; and/or phosphorylating the 5' end of the first portion of the second strand. In some instances, the amplifying step comprises hybridizing one or more amplification primers to the circularized second strand, and amplifying the circularized second strand with a polymerase.

In some instances, the determining step comprises sequencing all or part of the sequence of the amplified second strand to determining the location and the abundance of the analyte in the biological sample.

In some instances, the biological sample comprises a formalin-fixed, paraffin-embedded (FFPE) tissue sample, a fresh tissue sample, or a frozen tissue sample.

Also disclosed herein are kits. In some instances, the kits include (a) an array comprising a plurality of capture probes, wherein a capture probe of the plurality of capture probes comprises (i) a capture domain that hybridizes to an analyte of a biological sample and (ii) a spatial barcode; (b) one or more splint oligonucleotides and a ligase; (c) one or more RCA primers and a Phi29 DNA polymerase; (d) one or more restriction enzymes; and (e) instructions for performing any of the methods disclosed herein.

Also disclosed herein is a method of spatially detecting of an analyte in a biological sample comprising: (a) hybridizing the analyte to a capture probe comprising a spatial barcode and creating a second strand comprising a sequence that is complementary to a portion of the analyte and an extended capture probe; (b) denaturing the second strand under conditions wherein a first portion of the second strand and a second portion of the second strand de-hybridize from the extended capture probe; (c) hybridizing a splint oligonucleotide to the first portion and to the second portion; (d) ligating part of the splint oligonucleotide, to the first portion, and the second portion thereby creating a circularized second strand; (e) amplifying the circularized second strand, thereby creating an amplified second strand; and (f) determining all or part of the sequence of the amplified second strand to spatially detect the analyte in the biological sample.

Also disclosed herein is a method of spatially detecting of an analyte in a biological sample comprising: (a) hybridizing the analyte to a capture probe comprising a spatial barcode and creating a second strand comprising a sequence that is complementary to a portion of the analyte and an extended capture probe; (b) denaturing the second strand under conditions wherein a first portion of the second strand and a second portion of the second strand de-hybridize from the extended capture probe; (c) hybridizing a splint oligonucleotide to the first portion and to the second portion; (d) ligating part of the splint oligonucleotide, to the first portion, and the second portion thereby creating a circularized second strand; (e) amplifying the circularized second strand, thereby creating an amplified second strand; and (f) determining all or part of the sequence of the amplified second strand to spatially detect the analyte in the biological sample.

In some instances, the capture probe is on a substrate comprising a plurality of capture probes, wherein the capture probe comprises a capture domain and the spatial barcode, and wherein the analyte comprises a capture probe binding domain that is capable of binding to the capture domain. In some instances, the splint oligonucleotide comprises a backbone sequence, wherein the backbone sequence comprises a double-stranded sequence. In some instances, the methods further include extending the second portion using the splint oligonucleotide as a template, thereby creating an extended second portion. In some instances, the methods further include ligating the extended second portion to the first portion, thereby creating a circularized second strand. In some instances, the methods further include extending the capture probe, thereby creating an extended capture probe. In some instances, the methods further include amplifying the extended capture probe creating a second strand comprising a sequence that is complementary to a portion of the analyte and the extended capture probe. In some instances, the determined sequence of the amplified second strand comprises the spatial barcode or complementary sequence thereof for spatially detecting the analyte in the biological sample. In some instances, the splint oligonucleotide comprises a first sequence that is substantially complementary to the second portion, and a second sequence that is substantially complementary to the first portion. In some instances, the methods further include digesting the amplified second strand. In some instances, the method improves sensitivity of spatial detection of an analyte as compared to methods of spatially detecting an analyte that does not include rolling circle amplification.

Also disclosed herein is a method of spatially detecting of an analyte in a biological sample comprising: (a) hybridizing the analyte to a capture probe comprising a spatial barcode and extending the capture probe, thereby creating an extended capture probe; (b) amplifying the extended capture probe creating a second strand comprising a sequence that is complementary to a portion of the analyte and the extended capture probe; (c) hybridizing a splint oligonucleotide to a first portion of the second strand and a second portion of the second strand, (d) ligating part of the splint oligonucleotide, or a complement thereof, to the first portion and the second portion creating a circularized second strand; (e) amplifying the circularized second strand creating an amplified second strand and digesting the amplified second strand, thereby producing a plurality of second strand fragments; and (f) determining all or part of the sequence of a second strand fragment, and using the determined sequence to spatially detect the analyte in the biological sample. In some instances, the capture probe is on a substrate comprising a plurality of capture probes, wherein the capture probe comprises a capture domain and the spatial barcode, and wherein the analyte comprises a capture probe binding domain that is capable of binding to the capture domain. In some instances, the splint oligonucleotide comprises a backbone sequence, wherein the backbone sequence comprises a double-stranded sequence. In some instances, the methods further include denaturing the second strand under conditions wherein a first portion of the second strand and a second portion of the second strand de-hybridize from the extended capture probe. In some instances, the splint oligonucleotide comprises a first sequence that is substantially complementary to the second portion, and a second sequence that is substantially complementary to the first portion. In some instances, the determined sequence of the second strand fragment comprises the spatial barcode of the capture probe or a complementary sequence thereof.

In some instances, digesting comprises inducing a plurality of double-stranded breaks in the amplified second strand, wherein a double-stranded break occurs at a specific nucleic acid position(s) in the amplified second strand. In some instances, digesting comprises: hybridizing an oligonucleotide to a portion of the amplified second strand, thereby producing a double-stranded sequence, wherein the double-stranded sequence comprises a restriction site; and digesting the double-stranded sequence using a restriction enzyme. In some instances, the restriction site is added to the circularized second strand during the amplifying step. In some instances, the amplifying step comprises rolling circle amplification using the circularized second strand as a template. In some instances, a second strand fragment of the plurality of second strand fragments comprises all or part of the analyte or complement thereof and a spatial barcode or a complement thereof.

In some instances, the methods further include amplifying the second strand fragment prior to determining the sequence of the second strand fragment, thereby generating an amplified second strand fragment. In some instances, the methods further include determining the sequence of the amplified second strand fragment, wherein the determined sequence of the amplified second strand fragment comprises the spatial barcode sequence of the capture probe or a complementary sequence thereof, and using the determined sequence of the amplified second strand fragment or the spatial barcode to spatially detect the analyte in the biological sample. In some instances, the amplifying and digesting steps are performed concurrently.

In some instances, the oligonucleotide comprises a blocking moiety on the 3' end.

In some instances, the method improves sensitivity of spatial detection of an analyte as compared to methods of spatially detecting an analyte that do not include any method disclosed herein.

In some instances, the second portion of the second strand comprises one or more of a spatial barcode, a unique molecular identifier, and a primer sequence. In some instances, the second portion of the second strand comprises a portion of the captured analyte. In some instances, the first portion of the second strand comprises a primer sequence. In some instances, the first portion of the second strand comprises a portion of the captured analyte. In some instances, the splint oligonucleotide further comprises one or more of a functional sequence and a unique barcode. In some instances, the functional sequence is a primer sequence. In some instances, the primer is used for amplifying the circularized second strand.

In some instances, the ligating step comprises a T4 DNA ligase.

In some instances, the methods further include phosphorylating the 5' end of the double-stranded splint backbone sequence of the splint oligonucleotide prior to the ligation step. In some instances, the methods further include phosphorylating the 5' end of the first portion of the second strand.

In some instances, the capture domain comprises a sequence that is at least partially complementary to the analyte. In some instances, the capture domain of the capture probe comprises a homopolymeric sequence. In some instances, the capture domain of the capture probe comprises a poly(T) sequence. In some instances, the capture domain of the capture probe comprises a non-homopolymeric sequence. In some instances, the non-homopolymeric sequence is a random sequence, a partially random sequence or a fully defined sequence. In some instances, the capture probe comprises a cleavage domain. In some instances, the cleavage domain comprises a cleavable linker selected from a photocleavable linker, a UV-cleavable linker, an enzyme-cleavable linker, or a pH-sensitive cleavable linker. In some instances, extending the capture probe comprises reverse transcribing the analyte or complementary sequence thereof. In some instances, extending the capture probe comprises generating a sequence that is complementary to a portion of the analyte. In some instances, reverse transcribing the analyte generates a reverse complement of a template switching oligonucleotide. In some instances, amplifying the extended capture probe comprises annealing a template switching oligonucleotide primer to the reverse complement of the template switching oligonucleotide. In some instances, amplifying further comprises hybridizing the 3' end of the extended capture probe to the first portion of the second strand, and using the 3' end of the extended capture probe as a substrate in a rolling circle amplification reaction.

In some instances, the amplifying step (h) comprises: hybridizing one or more amplification primers to the circularized second strand, the capture probe, or the analyte; and amplifying the circularized second strand with a polymerase. In some instances, the determining step comprises sequencing. In some instances, the sequencing comprises generating a sequencing library of the amplified second strand, second strand fragments, or amplified second strand fragments.

In some instances, the biological sample comprises a FFPE sample. In some instances, the biological sample comprises a tissue section. In some instances, the biological sample comprises a fresh frozen sample. In some instances, the biological sample comprises live cells.

Also disclosed herein is a composition comprising the circularized second strand, wherein the circularized second strand comprises a first portion of the second strand, a portion of the second strand that remained hybridized to the extended capture probe, a second portion of the second strand, and a portion of the backbone sequence of the splint oligonucleotide.

Also disclosed herein is a kit, comprising: a substrate for spatial detection of an analyte, one or more splint oligonucleotides and a ligase; one or more RCA primers and a Phi29 DNA polymerase; and instructions for performing any of the methods disclosed herein.

Also disclosed herein is a kit, comprising: a substrate for spatial detection of an analyte; one or more splint oligonucleotides and a ligase; one or more RCA primers and a Phi29 DNA polymerase; one or more oligonucleotides and one or more restriction enzymes; and instructions for performing any of the methods disclosed herein.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
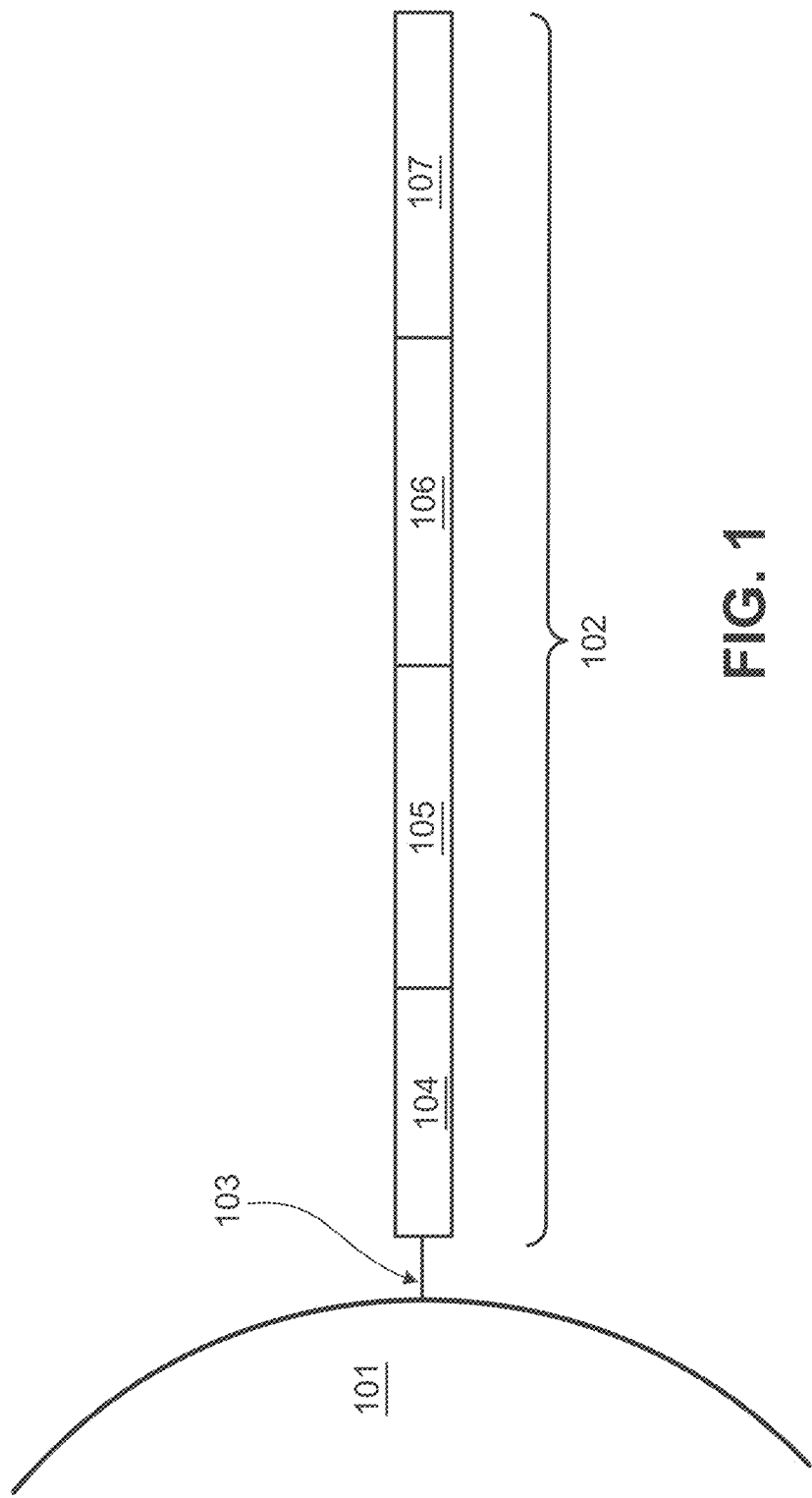
FIG. 1 is a schematic diagram showing an example of a barcoded capture probe, as described herein.

Disclosed herein are methods of improving sensitivity of spatial detection of an analyte in a biological sample. The techniques disclosed herein facilitate downstream processing by increasing the abundance of an analyte (e.g., increasing copies of an analyte or derivatives thereof) from a biological sample. For example, an analyte or an analyte derived molecule (e.g., a second strand cDNA molecule) is amplified prior to determining all or part of the sequence of the analyte. The amplification method described herein amplifies a spatial barcode of a capture probe or a complement thereof in addition to all or part of the sequence of an analyte or a complement thereof. This enables retention of spatial information. A splint oligonucleotide is hybridized to a first portion and a second portion of a second strand (e.g., a second strand cDNA molecule), where the second strand includes the spatial barcode or a complement thereof and all or part of the sequence of the analyte or a complement thereof. In some cases, hybridization of the splint oligonucleotide to the first portion and the second portion is enabled by denaturing the second strand hybridized to the extended capture probe under conditions that allow the first portion and the second portion to de-hybridize from the extended capture probe. The splint oligonucleotide mediates ligation of the second portion to the first portion of the second strand thereby producing a circularized second strand. The circularized second strand is amplified thereby creating an amplified second stand that includes the spatial information necessary (e.g., information including the sequence the analyte or a complement thereof and the sequence of spatial barcode or a complement thereof) to spatially detect the analyte in the biological sample. "Improving sensitivity" of spatial detection as used herein refers to an increased detection of an analyte at a location of a sample using methods disclosed herein compared to a reference sample.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination, and each of which is incorporated herein by reference in their entireties. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or part of sequencer specific flow cell attachment sequence (e.g., a P5 or P7 sequence), all or part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Exemplary methods for identifying spatial information of biological and/or medical importance can be found in U.S. Patent Application Publication No. 2021/0140982A1, U.S. Patent Application No. 2021/0198741A1, and/or U.S. Patent Application No. 2021/0199660.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in WO 2021/102003 and/or U.S. patent application Ser. No. 16/951,854, each of which is incorporated herein by reference in their entireties.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2021/102039 and/or U.S. patent application Ser. No. 16/951,864, each of which is incorporated herein by reference in their entireties.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, WO 2021/102005, and/or U.S. patent application Ser. No. 16/951,843, each of which is incorporated herein by reference in their entireties. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Surface Amplification on a Substrate to Improve Sensitivity of Spatial Detection This disclosure features methods of improving sensitivity of spatial detection of an analyte in a biological sample. In other methods of spatial analysis, after capture of an analyte on a capture probe affixed to an array, a second strand, which is complementary to the capture probe and to all or part of the analyte, is generated, followed by cDNA amplification, library preparation of the amplified secondary strand, and sequencing. The methods provided herein disclose an alternative method of spatial detection. In part, disclosed herein are methods using a splint oligonucleotide that can bind to a second strand (e.g., a second strand cDNA molecule bound to an analyte that is bound to a capture probe) and enable ligation of the second portion to the first portion thereby creating a circularized second strand. The circularized second strand can be amplified, all or part of the sequence of the amplified second strand can be determined, and the determined sequence used to spatially detect the analyte in the biological sample. This disclosure also features methods of improving sensitivity of spatial detection of an analyte in a biological sample using fragmentation (e.g., digestion) of the amplified second strand. In a non-limiting example, the method includes digesting the amplified second strand thereby generating second strand fragments, and determining all or part of the sequence of the second strand fragments to spatially detect the analyte in the biological sample.

This disclosure also features a method of improving sensitivity of spatial detection of an analyte in a biological sample where the method includes: providing a biological sample including an analyte on a substrate, wherein the substrate includes a plurality of capture probes comprising capture domains that are capable of hybridizing to an analyte sequence; hybridizing the analyte to the capture domain and creating a second strand including a sequence that is complementary to a portion of the analyte and the extended capture probe; hybridizing a splint oligonucleotide to a first portion of the second strand and to a second portion of the second strand; ligating part of the splint oligonucleotide, to the first portion, and the second portion thereby creating a circularized second strand; amplifying the circularized second strand, thereby creating an amplified second strand; and determining all or part of the sequence of the amplified second strand to spatially locate the analyte in the biological sample. In some embodiments, the method further includes extending the capture probe creating an extended capture probe. In some embodiments, the method further includes amplifying the extended capture probe creating a second strand including a sequence that is complementary to a portion of the analyte and the extended capture probe. In some embodiments, the method further includes subjecting the second strand to a denaturing step under conditions wherein the first portion of the second strand and the second portion of the second strand de-hybridize from the extended capture probe.

This disclosure also features a method of improving sensitivity of spatial detection of an analyte in a biological sample where the method includes: a biological sample including an analyte on a substrate wherein the substrate includes a plurality of capture probes comprising a capture domain, and wherein the analyte includes a capture probe binding domain that is capable of binding to the capture domain; hybridizing the capture probe binding domain to the capture domain and creating a second strand including a sequence that is complementary to a portion of the analyte and the extended capture probe; denaturing the second strand under conditions wherein a first portion of the second strand and a second portion of the second strand de-hybridize from the extended capture probe; hybridizing a splint oligonucleotide to the first portion and to the second portion; ligating part of the splint oligonucleotide, to the first portion, and the second portion thereby creating a circularized second strand; amplifying the circularized second strand, thereby creating an amplified second strand; and determining all or part of the sequence of the amplified second strand to spatially detect the analyte in the biological sample. In some embodiments, the method further includes extending the capture probe creating an extended capture probe. In some embodiments, the method further includes amplifying the extended capture probe creating a second strand including a sequence that is complementary to a portion of the analyte and the extended capture probe.

In some embodiments, the method further includes digesting the amplified second strand. In some embodiments, the amplifying step and the digesting step are performed in one reaction. For example, the method can include a step concurrently amplifying the circularized second strand creating an amplified second strand and digesting the amplified second strand, thereby producing a plurality of second strand fragments.

In a non-limiting example, this disclosure features a method improving sensitivity of spatial detection of an analyte in a biological sample where the method includes: a biological sample including an analyte on a substrate, wherein the substrate includes a plurality of capture probes comprising a capture domain, and wherein the analyte includes a capture probe binding domain that is capable of binding to the capture domain; hybridizing the capture probe binding domain to the capture domain and extending the capture probe creating an extended capture probe; amplifying the extended capture probe creating a second strand including a sequence that is complementary to a portion of the analyte and the extended capture probe; hybridizing a splint oligonucleotide to a first portion of the second strand and to a second portion of the second strand, ligating part of the splint oligonucleotide, or a complement thereof, to the first portion and the second portion creating a circularized second strand; concurrently amplifying the circularized second strand creating an amplified second strand and digesting the amplified second strand, thereby producing a plurality of second strand fragments; and determining all or part of the sequence of a second strand fragment, and using the determined sequence to spatially detect the analyte in the biological sample. In some embodiments, the method further includes subjecting the second strand to a denaturing step under conditions wherein a first portion of the second strand and a second portion of the second strand de-hybridize from the extended capture probe.

(a) Splint Oligonucleotide and Circularization of the Second Strand

This disclosure features methods for improving sensitivity of spatial detection of an analyte in a biological sample using a splint oligonucleotide hybridized to a second strand. In some embodiments, the method includes ligating part of the splint oligonucleotide to a first portion of the second strand and to a second portion of the second strand, thereby creating a circularized second strand. As used herein, a "splint oligonucleotide" refers to an oligonucleotide that has, at its 5' and 3' ends, sequences (e.g., a first sequence at the 5' end and a second sequence at the 3' end) that are complementary to portions (e.g., a first portion and a second portion) of the second strand. Upon hybridization to the first and second portions of the second strand, the splint oligonucleotide brings the two portions of the second strand into contact, allowing circularization of the second strand by ligation (e.g., ligation using any of the methods described herein). Upon hybridization to the first and second portions of the second strand, the second portion of the second strand is extended until the two portions of the second strand are brought into contact, allowing circularization of the second strand by ligation (e.g., ligation using any of the methods described herein). The ligation product can be referred to as the "circularized second strand." In some embodiments, after circularization of the second strand, rolling circle amplification can be used to amplify the circularized second strand creating an "amplified second strand."

In some embodiments, a first sequence of a splint oligonucleotide includes a sequence that is substantially complementary to a second portion of the second strand. In some embodiments, the second portion of the second strand is 3' to the first portion of the second strand. In some embodiments, the first sequence is at least 70% identical (e.g., at least 75% identical, at least 80% identical, at least 85% identical, at least 90% identical, at least 95% identical, or at least 99% identical) to the second portion.

In some embodiments, the splint oligonucleotide includes a backbone sequence. In some embodiments, the backbone sequence is double stranded while the first sequence and second sequences are single stranded. In some embodiments, the splint oligonucleotide is double stranded. In some embodiments, the backbone sequence includes a sequence that is substantially complementary to an amplification primer. The amplification primer can be a primer used in a rolling circle amplification reaction (RCA), where the RCA increases the "copy number" of the analyte and analyte derived molecules. In some embodiments, the backbone sequence includes a functional sequence. In some embodiments, the backbone sequence includes a restriction site. For example, the backbone sequence includes a sequence that is recognized by a restriction enzyme. In such cases, the backbone sequence can be converted from a single stranded sequence to a double stranded sequence (e.g., a double stranded sequence that includes a functional restriction site) by adding an oligonucleotide that is substantially complementary or by performing a nucleic acid extension reaction. In some embodiments, a double stranded backbone sequence includes a restriction site. In some instances, the restriction site is not in the captured analyte. In some instances, the restriction site is not in the genome of the biological sample.

In some embodiments, a second sequence of a splint oligonucleotide includes a sequence that is substantially complementary to a first portion of the second strand. In some embodiments, the first portion of the second strand is 3' to the second portion of the second strand. In some embodiments, the second sequence is at least 70% identical (e.g., at least 75% identical, at least 80% identical, at least 85% identical, at least 90% identical, at least 95% identical, or at least 99% identical) to the first portion.

In some embodiments, the splint oligonucleotide does not include a backbone sequence. In such cases, the first sequence and the second sequence are directly adjacent to each other on the splint oligonucleotide. As such, when the splint oligonucleotide is hybridized to the second strand, the first portion of the second strand and the second portion of the second strand hybridize to adjacent sequences on the splint oligonucleotide. This enables ligation without having to perform a gap filling step.

In some embodiments, the splint oligonucleotide includes a backbone sequence where the first sequence is not directly adjacent to the second sequence. In such cases, a "gap" exists on the splint oligonucleotide between where the first sequence is hybridized to the second portion and where the second sequence is hybridized to the first portion. In some embodiments, the splint oligonucleotide includes a sequence (e.g., a gap) between the first sequence and the second sequence of at least 1-100, 1-90, 1-80, 1-70, 1-60, 1-50, 1-40, 1-30, 1-20, 1-10, 1-9, 1-8, 1-7, 1-6, 1-5, 1-4, 1-3, 1-2 or 1 nucleotide(s). In a non-limiting example, a first sequence having a sequence that is substantially complementary to a second portion of the second strand and a second sequence having a sequence that is substantially complementary to a first portion of the second strand each bind to the second strand leaving a sequence (e.g., the "gap") in between the first and second sequences that is gap-filled thereby enabling ligation and generation of the circularized second strand. In some instances, to generate a splint oligonucleotide that includes a first sequence and a second sequence that are close enough to one another to initiate a ligation step, the second sequence is extended enzymatically (e.g., using a reverse transcriptase).

In some embodiments, the "gap" sequence between the first sequence and the second sequence include one nucleotide, two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, at least 25 nucleotides, at least 30 nucleotide, at least nucleotides, at least 40 nucleotides, at least 45 nucleotides, or at least 50 nucleotides.

In some embodiments, the gap is filled by extending the second portion of the second strand. In some embodiments, extending the second portion of the second strand includes a nucleic acid extension reaction (e.g., any of the nucleic acid extension reactions described herein). In some embodiments, extending the second portion of the second strand includes reverse transcribing the splint oligonucleotide. In some embodiments, extending the second portion of the second strand includes using a reverse transcriptase (e.g., any of the reverse transcriptases described herein). In some embodiments, extending the second portion of the second strand includes using a Moloney Murine Leukemia Virus (M-MulV) reverse transcriptase. In some embodiments, the reverse transcriptase includes strand displacement properties. In some embodiments, extending the second portion of the second strand generates a sequence that is complementary to the splint oligonucleotide. In some embodiments, extending the second portion of the second strand generates an extended second sequence of the second strand that is complementary to the splint oligonucleotide. In some embodiments, extending the second portion of the second strand generates a sequence that is adjacent to the first portion of the second strand.

In some embodiments, the ligation step includes ligating the second portion to the first portion of the second strand using enzymatic or chemical ligation. In some embodiments where the ligation is enzymatic, the ligase is selected from a T4 RNA ligase (Rnl2), a SplintR ligase, a single stranded DNA ligase, or a T4 DNA ligase. In some embodiments, the ligase is a T4 RNA ligase (Rnl2) ligase. In some embodiments, the ligase is a pre-activated T4 DNA ligase as described herein. A non-limiting example describing methods of generating and using pre-activated T4 DNA include U.S. Pat. No. 8,790,873, the entire contents of which are herein incorporated by reference.

(b) Amplification of Circularized Second Strand

This disclosure features methods for improving sensitivity of spatial detection of an analyte in a biological sample by amplifying the circularized second strand. In a non-limiting example, the method includes an amplifying step wherein one or more amplification primers are hybridized to the circularized second strand and the circularized second strand is amplified using a polymerase. In another non-limiting example, the method includes an amplifying step where a 3' end of the extended capture probe is used as a primer and the circularized second strand is amplified using a polymerase. In some embodiments, the amplifying step increases the copy number of the second strand. The sequence of the amplified second strand can then be determined and used to spatially detect the analyte in the biological sample. In some embodiments, the amplifying step includes rolling circle amplification (RCA).

As used herein, rolling circle amplification (RCA) can refer to a polymerization reaction carried out using a single-stranded circular DNA (e.g., a circularized second strand) as a template and an amplification primer that is substantially complementary to the single-stranded circular DNA (e.g., the circularized second strand) to synthesize multiple continuous single-stranded copies of the template DNA (e.g., the circularized second strand). In some embodiments, RCA includes hybridizing one or more amplification primers to the circularized second strand and amplifying the circularized strand using a Phi29 DNA polymerase. In addition, RCA can refer to a polymerization reaction carried out using a single-stranded circular DNA (e.g., a circularized second strand) as a template and the 3' end of the extended capture probe as a primer to synthesize multiple continuous single-stranded copies of the template DNA (e.g., the circularized second strand). In such cases, the 3' end of the extended capture is substantially complementary to a portion (e.g., a portion corresponding to the first portion of the second strand) of the single-stranded circular DNA (e.g., the circularized second strand). For example, RCA can include hybridizing the 3' end of the extended capture probe to the circularized second strand and amplifying the circularized strand using a Phi29 DNA polymerase.

In some embodiments, an amplification primer includes a sequence that is substantially complementary to the first portion or the second portion of the circularized second strand. For example, the amplification primer can be substantially complementary to the first portion or a complement thereof. By substantially complementary, it is meant that the amplification primer is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in the circularized second strand.

In some embodiments, the amplifying step includes hybridizing the 3' end of the extended capture probe to the first portion of the second strand, and using the 3' end of the extended capture probe as a substrate in a rolling circle amplification (RCA) reaction. In such cases, the method includes a denaturing step under conditions where the 3' end of the extended capture probe is de-hybridized from the first portion of the second strand. During the subsequent processing of the second strand (e.g., ligation and circularization) the second strand can remain hybridized to the extended capture probe. Therefore, the 3' end of the extended capture probe can be re-hybridized to the first portion of the second strand.

In some embodiments, non-limiting examples of DNA polymerase include: Bsu DNA polymerase, Bst DNA polymerase, VENT™ DNA polymerase, DEEPVENT™ DNA polymerase, Phi29 DNA polymerase, Klenow fragment, T4 DNA polymerase and T7 DNA polymerase enzymes. In some embodiments, the DNA polymerase is Phi29 DNA polymerase. In some embodiments, the term "DNA polymerase" includes not only naturally-occurring enzymes but also all modified derivatives thereof, including derivatives of naturally-occurring DNA polymerase enzymes. For instance, in some embodiments, the DNA polymerase is modified to remove 5'-3' exonuclease activity. Sequence-modified derivatives or mutants of DNA polymerase enzymes that can be used include, but are not limited to, mutants that retain at least some of the functional, e.g., DNA polymerase activity of the wild-type sequence.

(c) Capture Probe Extension, Second Strand Synthesis and De-hybridizing

This disclosure features methods for improving sensitivity of spatial detection of an analyte in a biological sample using de-hybridization of a second strand, hybridization of a splint oligonucleotide, circularization of the second strand, and amplification of a circularized second strand. In a non-limiting example, the method includes capturing an analyte, extending a capture probe, generating a second strand, de-hybridizing a first and second portion of the second strand, hybridizing a splint oligonucleotide to the second strand, circularizing the second strand and amplifying the circularized second strand.

In some embodiments, extending the capture probe includes performing a nucleic acid extension reaction. In some embodiments, extending the capture probe includes reverse transcribing the analyte or complementary sequence thereof. In some embodiments, extending the capture probe includes generating a sequence that is complementary to a portion of the analyte. In some embodiments, extending the capture probe includes attaching a template switching oligonucleotide to the analyte. In some embodiments, reverse transcribing the analyte generates a reverse complement of a template switching oligonucleotide.

In some embodiments, amplifying the extended capture probe includes annealing a template switching oligonucleotide (TSO) primer to a reverse complement of the template switching oligonucleotide (rcTSO). In some embodiments, extending the capture probe and/or amplifying the extended capture probe includes using a polymerase. A non-limiting example of a polymerase is a DNA polymerase.

In some embodiments, extending the capture probe includes a reverse transcriptase enzyme, where the enzyme includes one or more of terminal transferase activity, template switching ability, strand displacement ability, or combinations thereof. In some embodiments, the terminal transferase activity of the reverse transcriptase adds untemplated nucleotides to the 3' end of the cDNA molecule. In some embodiments, the reverse transcriptase adds 1, 2, 3, 4, 5, 6, 7, 8, 9, 10, or more untemplated nucleotides to the 3' end of the cDNA molecule. In some embodiments the first enzyme includes a Moloney Murine Leukemia Virus (M-MLV) reverse transcriptase enzyme. In some embodiments the first enzyme includes a Moloney Murine Leukemia Virus (M-MLV) reverse transcriptase enzyme and the second enzyme is a Bst DNA polymerase. In some embodiments the first enzyme includes a Moloney Murine Leukemia Virus (M-MLV) reverse transcriptase enzyme and the second enzyme is a Phi29 DNA polymerase.

In some embodiments, second strand synthesis is performed by a DNA polymerase selected from the group including, but not limited to: E.coli DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes. In some embodiments, the second strand synthesis is a Phi29 DNA polymerase. In some embodiments, the second strand synthesis is performed by a Bst DNA polymerase.

In some embodiments, the method includes contacting the analyte bound to the capture probe with a composition that includes a template switching oligonucleotide (TSO). In some embodiments, the TSO includes an untemplated nucleotide region and a TSO primer region. In some embodiments, the length of a template switching oligonucleotide can be at least about 1, 2, 20, or 50 nucleotides or longer. In some embodiments, the length of a template switching oligonucleotide can be at most about 2, 10, 20, 50, 100, 150, 200, or 250 nucleotides or longer.

In some embodiments, the TSO primer region includes a sequence that is at least partially complementary to the TSO primer. In some embodiments, the TSO primer region includes a sequence that is 1, 2, 3, 4, 5, 6, 7, 8, 9, 10, 11, 12, 13, 14, 15, 16, 17, 18, 19, 20, 21, 22, 23, 24, or nucleotides in length. In some embodiments, the untemplated nucleotide region includes a sequence that is at least partially complementary to the untemplated nucleotides added on to the 3' end of the extended capture probe. In some embodiments, the untemplated nucleotide region includes a sequence that is 1, 2, 3, 4, 5, 6, 7, 8, 9, 10, or more nucleotides in length.

In some embodiments, the untemplated nucleotide region includes a series of G bases to complement the overhanging C bases at the 3' end of a cDNA molecule. In some embodiments, the series of G bases can include 1 G base, 2 G bases, 3 G bases, 4 G bases, 5 G bases, or more than 5 G bases. In some embodiments, the hybridization region can include at least one base in addition to at least one G base. In other embodiments, the hybridization can include bases that are not a G base. In some embodiments, the template region and hybridization region are separated by a spacer. In some embodiments, the reverse complement of the TSO (rcTSO) is incorporated at the 3' end of the cDNA molecule when the TSO binds to the untemplated nucleotides on the cDNA molecule and the reverse transcriptase reverse transcribes the TSO.

In some embodiments, the method includes contacting the analyte bound to the capture probe with a composition that includes a TSO primer. In some embodiments, the TSO primer includes a sequence that is at least partially complementary to the rcTSO sequence. In some embodiments, the TSO primer includes a sequence that is 1, 2, 3, 4, 5, 6, 7, 8, 9, 10, 11, 12, 13, 14, 15, 16, 17, 18, 19, 20, 21, 22, 23, 24, 25, or nucleotides in length. In some embodiments, the TSO primer includes any of the deoxyribonucleic acids, ribonucleic acids, modified nucleic acids, or any combination therein (e.g., any of the nucleotide derivatives or combinations thereof described herein). In some embodiments, the TSO primer includes RNA bases. In some embodiments, the TSO primer does not include RNA bases.

In some embodiments, the TSO primer is a single-stranded nucleic acid where the 3' end is used as a chemical substrate for a nucleic acid polymerase in a nucleic acid extension reaction. In some embodiments, the TSO primer is used as a chemical substrate for a second strand synthesis where the extended capture probe is used as a template in a nucleic acid extension reaction, where the second strand is complementary to all or a portion of the cDNA molecule and all or a portion of the capture probe. In some embodiments, the TSO primer and a first enzyme (e.g., a reverse transcriptase with DNA polymerase functionality) are used in second strand synthesis, where the second strand synthesis occurs in the same reaction as the reverse transcription. In some embodiments, the TSO primer and a second enzyme (e.g., a DNA polymerase) are used in a second strand synthesis reaction, where the second strand synthesis occurs in the same reaction as the reverse transcription.

In some embodiments, the method includes contacting the analyte bound to the capture probe with a composition that includes a TSO blocking moiety. In some embodiments, the TSO blocking moiety is a nucleotide sequence that is 1, 2, 3, 4, 5, 6, 7, 8, 9, 10, 11, 12, 13, 14, 15, 16, 17, 18, 19, 20, 21, 22, 23, 24, 25, or nucleotides in length. In some embodiments, the TSO blocking moiety is a nucleotide sequence that is at least partially complementary to the TSO. In some embodiments, the TSO blocking moiety prohibits the TSO primer from interacting with the rcTSO. For example, the TSO blocking moiety can bind to the TSO primer thereby inhibiting the TSO primer from interacting the rcTSO. In some embodiment the TSO blocking moiety is a nucleotide sequence that is at least partially complementary to the rcTSO. In some embodiments, the TSO blocking moiety prohibits the rcTSO from interacting with the TSO primer. For example, the TSO blocking moiety can bind to the rcTSO thereby inhibiting the rcTSO from interacting with the TSO primer.

This disclosure features methods of improving sensitivity of spatial detection of an analyte in a biological sample where a second strand is circularized by denaturing the second strand under conditions wherein a first portion of the second strand and a second portion of the second strand de-hybridize from the extended capture probe and are hybridized to a splint oligonucleotide, ligated (e.g., circularized), and amplified.

In some embodiments, denaturing includes temperature modulation. For example, a first portion and a second portion have predetermined annealing temperatures based on the nucleotide composition (A, G, C, or T) within the known sequence. In some embodiments, the temperature is modulated up to 5° C., up to 10° C., up to 15° C., up to 20° C., up to 25° C., up to 30° C., or up to 35° C. above the predetermined annealing temperature. In some embodiments, the temperature is modulated at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35° C. above the predetermined annealing temperature. In some embodiments, once the temperature is modulated to a temperature above the predetermined annealing temperature, the temperature is cooled down to the predetermined annealing temperature at a ramp rate of about 0.1° C./second to about 1.0° C./second (e.g., about 0.1° C/second to about 0.9° C./second, about 0.1° C./second to about 0.8° C./second, about 0.1° C/second to about 0.7° C./second, about 0.1° C./second to about 0.6° C./second, about 0.1° C/second to about 0.5° C./second, about 0.1° C./second to about 0.4° C./second, about 0.1° C/second to about 0.3° C./second, about 0.1° C./second to about 0.2° C./second, about 0.2° C/second to about 1.0° C./second, about 0.2° C./second to about 0.9° C./second, about 0.2° C/second to about 0.8° C./second, about 0.2° C./second to about 0.7° C./second, about 0.2° C/second to about 0.6° C./second, about 0.2° C./second to about 0.5° C./second, about 0.2° C/second to about 0.4° C./second, about 0.2° C./second to about 0.3° C./second, about 0.3 to about 1.0° C./second, about 0.3° C./second to about 0.9° C./second, about 0.3° C./second to about 0.8° C/second, about 0.3° C./second to about 0.7° C./second, about 0.3° C./second to about 0.6° C/second, about 0.3° C./second to about 0.5° C./second, about 0.3° C./second to about 0.4° C./second, about 0.4° C./second to about 1.0° C./second, about 0.4° C./second to about 0.9° C/second, about 0.4° C./second to about 0.8° C./second, about 0.4° C./second to about 0.7° C/second, about 0.4° C./second to about 0.6° C./second, about 0.4° C./second to about 0.5° C/second, about 0.5° C./second to about 1.0° C./second, about 0.5° C./second to about 0.9° C/second, about 0.5° C./second to about 0.8° C./second, about 0.5° C/second to about 0.7° C./second, about 0.5° C./second to about 0.6° C/second, about 0.6° C./second to about 1.0° C/second, about 0.6° C./second to about 0.9° C./second, about 0.6° C./second to about 0.8° C/second, about 0.6° C./second to about 0.7° C./second, about 0.7° C./second to about 1.0° C/second, about 0.7° C./second to about 0.9° C./second, about 0.7° C./second to about 0.8° C./second, about 0.8° C./second to about 1.0° C./second, about 0.8° C./second to about 0.9° C/second, or about 0.9° C./second to about 1.0° C./second).

In some embodiments, denaturing includes temperature cycling. In some embodiments, denaturing includes alternating between denaturing conditions (e.g., a denaturing temperature) and non-denaturing conditions (e.g., annealing temperature).

(d) Digestion of the Amplified Second Stand and Amplification of the Fragments

This disclosure features methods of improving sensitivity of spatial detection of an analyte in a biological sample where the method includes digesting (or fragmenting) an amplified second strand to produce second strand fragments. In a non-limiting example, the digesting step includes inducing a plurality of double-stranded breaks in an amplified second strand. In some embodiments, the double-stranded break occurs at a specific nucleic acid position. In some embodiments, the second strand fragment includes a sequence of the second strand or a complement thereof and a sequence of the spatial barcode or a complement thereof.

In some embodiments, a double stranded break is induced using a restriction enzyme and a restriction site. In such cases because the product of an RCA reaction is a continuous single-stranded molecule (e.g., amplified second strand), a portion of the single-stranded molecule (e.g., amplified second strand) is made into a double stranded molecule. In some embodiments, the single-stranded molecule is converted into a double stranded molecule by contacting the single-stranded molecule with an oligonucleotide that is substantially complementary to a portion of the single-stranded molecule (e.g., amplified second strand) and includes a sequence that can serve as a restriction site for a restriction enzyme.

In some embodiments, the restriction site is not present in the sequence of the analyte bound to the capture probes. In such cases, when the amplified second strand is contacted with the oligonucleotide and the restriction enzyme, the oligonucleotide will not hybridize to the portion of the second strand that includes a sequence derived from the analyte. In some embodiments, the restriction site sequence is present in the second portion of the second strand.

In some embodiments, the digesting step includes contacting the amplified second strand with an oligonucleotide, where upon hybridization forms a double-stranded sequence with the amplified second strand. In some embodiments, the oligonucleotide includes one nucleotide, two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, at least 25 nucleotides, at least 30 nucleotide, at least 35 nucleotides, at least 40 nucleotides, at least 45 nucleotides, or at least 50 nucleotides. In some embodiments, the oligonucleotide is substantially complementary to a portion of the amplified second strand. By substantially complementary, it is meant that the oligonucleotide is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in the amplified second strand. In some embodiments, following digestion, the residual oligonucleotide that remains hybridized. In some embodiments, following digestion, the oligonucleotide is de-hybridized from the amplified second strand.

In some embodiments, the oligonucleotide includes a 3' blocking moiety. The 3' blocking moiety prevents the oligonucleotide from being used as a primer in an RCA reaction. In some embodiments, the free 3' end of the oligonucleotide can be blocked by chemical modification, e.g., addition of an azidomethyl group as a chemically reversible capping moiety such that the capture probes do not include a free 3' end. Non-limiting examples of 3' modifications include dideoxy C-3' (3'-ddC), 3' inverted dT, 3' C3 spacer, 3'Amino, and 3' phosphorylation.

In some embodiments where the digesting step includes digesting the amplified second strand with a restriction enzyme, the restriction enzyme can induce a blunt end or sticky end (e.g., not a blunt end) break. In cases where digestion results in one or more blunt ends, the second strand fragments that include the blunt ends can be dephosphorylated (e.g., Shrimp Alkaline Phosphatase (SAP)) so that the ends do not reanneal or anneal to another blunt ended second strand fragment.

In some embodiments, the restriction enzyme is a rare-cutting restriction endonuclease. A rare-cutting restriction endonuclease includes a restriction site about once per 10 kilobases (kb), about once per 20 kb, about once per 30 kb, about once per 40kb, once per 50 kb, about once per 60 kb, about one per 70 kb, about once per 80 kb, about once per 90 kb, about once per 100kb, about once per 200 kb, about once per 300 kb, about once per 400 kb, about once per 500 kb, about once per 750kb, or about once per 1 megabase (mb) of gDNA. In some embodiments, the restriction enzymes includes restriction enzymes with a 6-bp restriction site or an 8-bp restriction site. Non-limiting examples of restriction enzymes that can be used to digest the amplified second strand, include NotI, SalI, SfiI, NruI, MluI, SacII, and BssHII. In some embodiment, the restriction enzymes is NotI. In some embodiments, the restriction enzyme is SfiI. In some embodiments, the restriction enzyme can be a non-naturally occurring restriction enzyme.

Non-limiting examples of other methods for inducing a double-stranded DNA break include target specific nucleases (e.g., a CRISPR/Cas system where a Cas nuclease is directed to a specific sequence on the amplified second strand).

In some embodiments, the method further includes amplifying the second strand fragment, thereby generating an amplified second strand fragment(s). In some embodiments, amplifying the second strand fragments includes circle-to-circle amplification as described in Dahl et al. PNAS, 101(13): 4548-4553 (2004), the entire contents of which are incorporated herein by reference. In some embodiments, the method further includes determining the sequence of the amplified second strand fragment, wherein the determined sequence of the amplified second strand fragment includes the spatial barcode sequence of the capture probe or a complementary sequence thereof, and using the determined sequence of the amplified second strand fragment or the spatial barcode to spatially detect the analyte in the biological sample.

(e) Slides, Biological Samples, and Analytes

This disclosure features a method for identifying a location of an analyte in a biological sample using a substrate (e.g., a first substrate) that includes a plurality of capture probes, where a capture probe of the plurality of capture probes include a capture domain but no spatial barcode. In some embodiments, the capture probe is affixed to the substrate at a 5' end. In some embodiments, the plurality of capture probes are uniformly distributed on a surface of the substrate. In some embodiments, the plurality of capture probes are located on a surface of the substrate but are not distributed on the substrate according to a pattern. In some embodiments, the substrate (e.g., a second substrate) includes a plurality of capture probes, where a capture probe of the plurality of capture probes includes a capture domain and a spatial barcode.

In some embodiments, the capture domain includes a sequence that is at least partially complementary to the analyte or the analyte derived molecule. In some embodiments, the capture domain of the capture probe includes a poly(T) sequence. In some embodiments, the capture domain includes a functional domain. In some embodiments, the functional domain includes a primer sequence. In some embodiments, the capture probe includes a cleavage domain. In some embodiments, the cleavage domain includes a cleavable linker from the group consisting of a photocleavable linker, a UV-cleavable linker, an enzyme-cleavable linker, or a pH-sensitive cleavable linker.

In some embodiments, the capture domain of the capture probe includes a non-homopolymeric sequence. In some embodiments, the capture domain is a defined sequence. In such cases, the defined sequence can be substantially complementary to a portion of the amplified padlock oligonucleotide. When the capture probe is substantially complementary to a portion of the amplified oligonucleotide, the capture domain can be used to capture all or a portion of the padlock oligonucleotide. In some instances, a defined sequence is about 5 to 50 nucleotides in length (e.g., about 5 to 25, about 5 to 20, about 10 to 25, about 10 to 20). In some instances, the length of the defined sequence is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides long. Defined sequences can include natural or synthetic nucleic acids. It is appreciated that a skilled artisan can design the defined sequence in order to capture a particular target or particular targets of interest.

In some embodiments, the capture domain of the capture probe includes a random sequence. In some embodiments, the capture domain includes a non-random sequence. For example, a capture domain with a non-random sequence can include, without limitation, a defined sequence or a homopolymeric sequence.

In some embodiments, the biological sample includes a FFPE sample. In some embodiments, the biological sample includes a tissue section. In some embodiments, the biological sample includes a fresh frozen sample. In some embodiments, the biological sample includes live cells.

The methods provided herein can be applied to analyte or analyte derived molecules including, without limitation, a second strand cDNA molecule ("second strand"). In some embodiments, the analyte or analyte derived molecules include RNA and/or DNA.

(f) Compositions and Kits

In some instances, disclosed herein are compositions and kits that are used to carry out the methods described herein. In some embodiments, the kit includes a splint oligonucleotide and a ligase (e.g., a T4 DNA ligase (Rnl2), a SplintR ligase, a single stranded DNA ligase, or a T4 DNA ligase). In some embodiments, the kit further includes one or more amplification primers (e.g., two or more primers, three or more primers, four or more primers, five or more primers, six or more primers, seven or more primers, eight or more primers, nine or more primers, or ten or more primers) and a polymerase (e.g., a Phi29 DNA polymerase). In some embodiments, the kit further includes an oligonucleotide and a restriction enzyme (e.g., any of the exemplary restriction enzymes described herein).

In some embodiments, the kit further includes a first substrate including a plurality of capture probes, wherein a capture probe of the plurality includes and a capture domain, wherein the analyte is capable of hybridizing to the capture domain. It is appreciated that the kit can include any of the elements of the substrate, array, or capture probes as described herein.

In some embodiments, a kit used to carry out the methods described herein includes: a substrate for spatial detection of an analyte; one or more splint oligonucleotides and a ligase; one or more RCA primers and a Phi29 DNA polymerase; and instructions for performing any of the methods described herein.

In some embodiments, a kit used to carry out the methods described herein includes: a substrate for spatial detection of an analyte; one or more splint oligonucleotides and a ligase; one or more RCA primers and a Phi29 DNA polymerase; one or more oligonucleotides and one or more restriction enzymes; and instructions for performing any of the methods described herein.

This disclosure features compositions including the circularized second strand, wherein the circularized second strand includes a first portion of the second strand, a portion of the second strand that remained hybridized to the extended capture probe, a second portion of the second strand, and a portion of the backbone sequence of the splint oligonucleotide.

EXAMPLES

EXAMPLE 1

Method for Improving Sensitivity of Spatial Detection of an Analyte

This example provides an exemplary method for improving sensitivity of spatial detection of an analyte in a biological sample. In a non-limiting example, the method includes: hybridizing the analyte to a capture probe, creating a second strand that is complementary to a portion of the analyte and the extended capture probe, denaturing the second strand under conditions where a first portion of the second strand and a second portion of the second strand de-hybridize from the extended capture probe; hybridizing a splint oligonucleotide to the partially denatured second strand and using the split oligonucleotide to ligate the first and second portions together, thereby creating a circularized second strand; amplifying the circularized second strand, thereby creating an amplified second strand; and determining all or part of the sequence of the amplified second strand to spatially detect the analyte in the biological sample.

Briefly, a sample (e.g., an FFPE sample) is decrosslinked to remove formaldehyde crosslinks within the sample thereby releasing the analytes for spatial detection. The tissue samples are incubated with an HCl solution for 1 minute, repeated twice for a total of 3 minutes. Following HCl incubations, the tissue sections are incubated at 70° C. for 1 hour in TE pH 9.0. TE is removed and the tissues are incubated in 1xPBS-Tween for 15 minutes.

Figure 2:
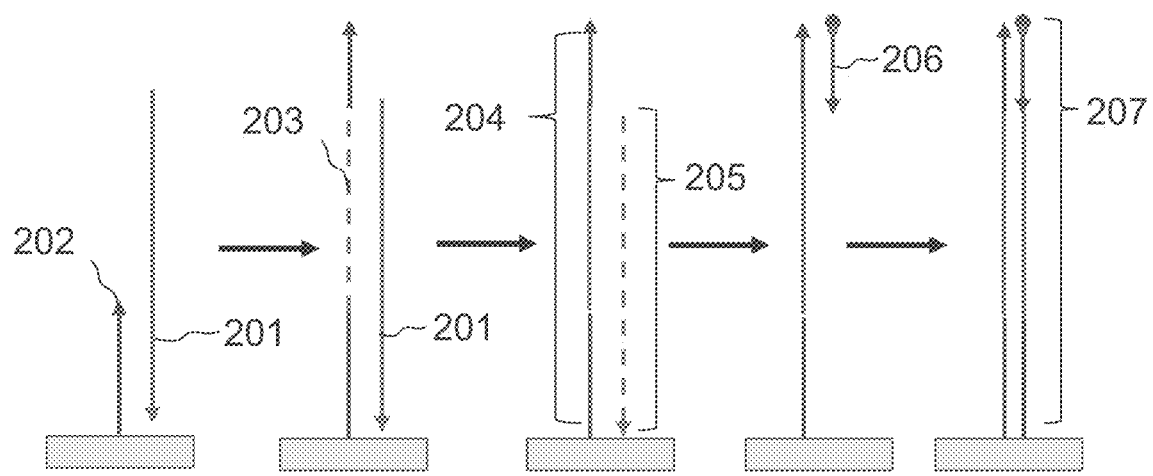
FIG. 2 is a schematic illustrating exemplary, non-limiting, non-exhaustive steps for second strand synthesis.

FIG. 2 shows exemplary, non-limiting, steps for second strand synthesis. The analyte 201 is hybridized to a capture probe 202 via a capture probe binding domain. A nucleic acid extension reaction (indicated by the dotted line and numeral 203) using a DNA polymerase is used to extend the capture probe thereby creating an extended capture probe 204. The analyte is removed (indicated by the dotted line and numeral 205) from the extended capture probe. A second strand synthesis primer 206 is hybridized to the extended capture probe. The extended capture probe is then copied using the second strand synthesis primer, thereby creating a second strand 207 that includes a sequence of the analyte or a complement thereof and the sequence of the spatial barcode or a complement thereof. The second strand remains hybridized to the extended capture probe.

Figure 3A:
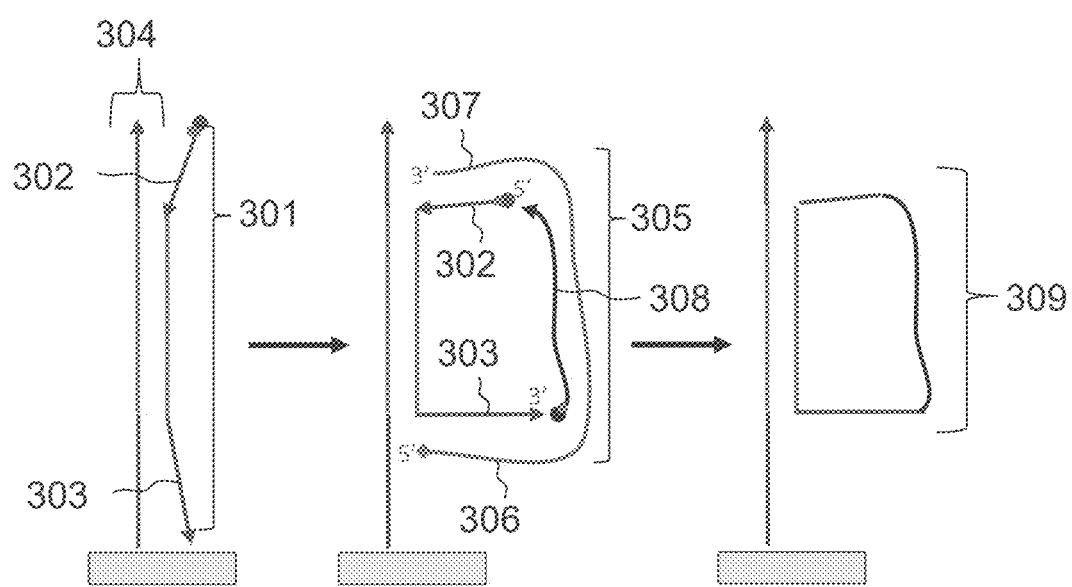
FIG. 3A is a schematic illustrating exemplary, non-limiting, non-exhaustive steps for generating a circularized second strand.

As show in FIG. 3A, the second strand 301 is denatured under conditions where a first portion 302 of the second strand and a second portion 303 of the second strand de-hybridize from the extended capture probe 304. Denaturing conditions include heating the second strand to 10° C. above the predetermined annealing temperature for 5 min and cooling at a rate of 0.5° C/second back down to the predetermined annealing temperature.

The splint oligonucleotide 305 includes a first sequence 306 that is substantially complementary to the second portion 303, and a second sequence 307 that is substantially complementary to the first portion 302. Following de-hybridizing of the first portion 302 and second portion 303, a splint oligonucleotide 305 is hybridized to the first portion 302 and the second portion 303.

The splint oligonucleotide mediates ligation between the second portion and the first portion, thereby creating a circularized second strand. Briefly, a nucleic acid extension reaction 308 is used to extend the second portion of the second strand in order to place the second portion directly adjacent to the first portion by using the middle section of the splint oligonucleotide as the template. The second portion is ligated to the first portion, thereby creating a circularized second strand 309.

Figure 3B:
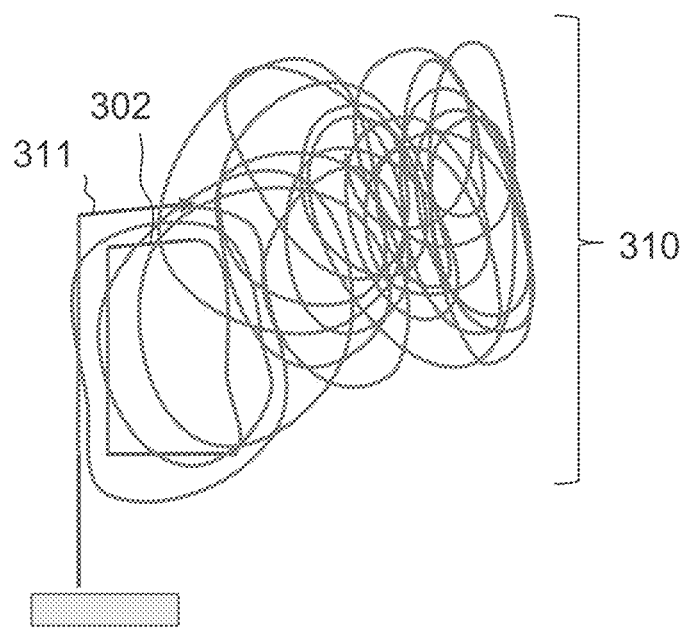
FIG. 3B is a schematic illustrating exemplary, non-limiting, non-exhaustive steps for amplifying a circularized second strand.

As shown in FIG. 3B, the circularized second strand is amplified to create an amplified second strand 310. Amplification includes rolling circle amplification where the 3' end of the extended capture probe 311 is hybridized to the circularized second strand (e.g., the first portion 302 of the second strand included in the circularized second strand). Finally, all or part of the sequence of the amplified second strand is sequenced and the sequence is used to determine the spatial location of the analyte in the biological sample.

EXAMPLE 2

Figure 4:
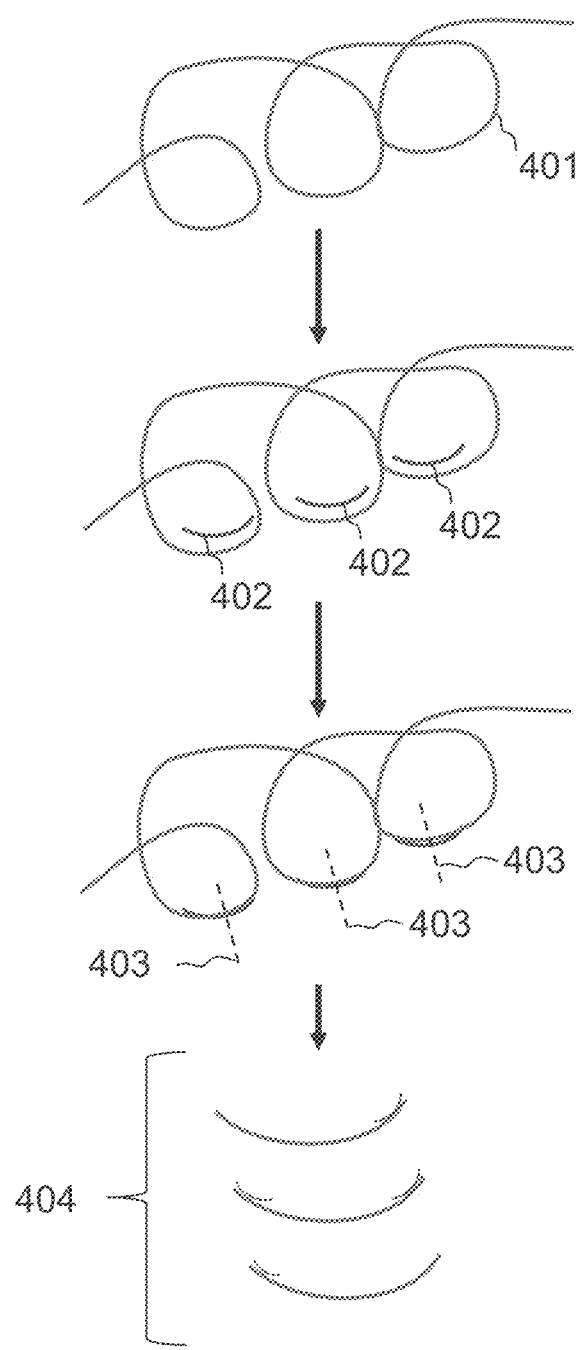
FIG. 4 is a schematic illustrating exemplary, non-limiting, non-exhaustive steps for digesting an amplified second strand using oligonucleotides, partially double stranded amplified second strands, and a restriction enzyme.

Digestion of the Amplified Second Strand and Analysis of Second Strand Fragments This example provides an exemplary method for improving sensitivity of spatial detection of an analyte in a biological sample. In a non-limiting example, the method includes digesting an amplified second strand thereby generating second strand fragments. As shown in FIG. 4, the amplified second strand 401 is contacted with an oligonucleotide 402 where the oligonucleotide includes a sequence that is substantially complementary to a portion of the amplified second strand. Hybridizing the oligonucleotide to the amplified second strand creates one or more double stranded restriction sites in the amplified second strand. The amplified second strand including the restriction site is contacted with a restriction enzyme that generates double-stranded breaks (as indicated by the dashed line and numeral 403). The double stranded breaks create restriction enzyme fragments of the amplified second strand, thereby creating second strand fragments 404. All or part of the sequence of the fragments of the amplified second strand (e.g., the second strand fragments) is determined and used to spatially detect the analyte in the biological sample.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A method of determining location of an analyte in a biological sample, the method comprising:
    (a) hybridizing the analyte to a capture probe on an array, wherein the capture probe comprises a spatial barcode and a capture domain;
    (b) extending the capture probe using the analyte as a template, thereby generating an extended capture probe, and generating a second strand comprising a sequence that is complementary to (i) the analyte or a complement thereof and (ii) the spatial barcode or a complement thereof, wherein the second strand is generated using a second strand synthesis primer;
    (c) denaturing the second strand from the extended capture probe under conditions wherein a 5' end of the second strand and a 3' end of the second strand dehybridize from the extended capture probe;
    (d) hybridizing a splint oligonucleotide both to the 5' end of the second strand and to the 3' end of the second strand;
    (e) generating a circularized second strand;
    (f) amplifying the circularized second strand, thereby creating an amplified second strand; and
    (g) determining all or part of the sequence of the amplified second strand to determine the location of the analyte in the biological sample.

2. The method of claim 1, wherein the analyte comprises a capture domain capture sequence that hybridizes to the capture domain, and wherein the capture domain comprises a poly(T) sequence.

3. The method of claim 2, wherein the capture domain capture sequence comprises a poly(A) sequence.

4. The method of claim 1, wherein the array comprises a plurality of capture probes.

5. The method of claim 1, wherein extending the capture probe and generating a second strand utilize a polymerase or reverse transcriptase.

6. The method of claim 1, wherein denaturing comprises increasing the temperature, thereby dehybridizing the 5' end of the second strand and the 3' end of the second strand from the extended capture probe.

7. The method of claim 1, further comprising, before step (e), extending the 3' end of the second strand using the splint oligonucleotide as a template, thereby creating an extended 3' end.

8. The method of claim 7, wherein generating the circularized second strand comprises ligating the extended 3' end to the 5' end using a ligase.

9. The method of claim 1, wherein amplifying the circularized second strand comprises rolling circle amplification (RCA) using the circularized second strand as a template.

10. The method of claim 1, wherein the amplified second strand comprises (i) the spatial barcode or complement thereof and (ii) all or part of the analyte or a complement thereof.

11. The method of claim 1, further comprising hybridizing an oligonucleotide to a portion of the amplified second strand, thereby producing a double-stranded sequence, and wherein the double-stranded sequence comprises a restriction site.

12. The method of claim 11, further comprising digesting the double-stranded sequence using a restriction enzyme.

13. The method of claim 1, wherein the splint oligonucleotide comprises a first sequence that is substantially complementary to the 5' end of the second strand, and a second sequence that is substantially complementary to the 3' end of the second strand.

14. The method of claim 1, wherein the capture probe further comprises one or more functional domains, a unique molecular identifier, a cleavage domain, and combinations thereof.

15. The method of claim 1, further comprising phosphorylating the 5' end of the splint oligonucleotide prior to the ligation step, and/or phosphorylating the 5' end of the second strand.

16. The method of claim 1, wherein the amplifying step comprises hybridizing one or more amplification primers to the circularized second strand, and amplifying the circularized second strand with a polymerase.

17. The method of claim 1, wherein the determining step comprises sequencing all or part of the sequence of the amplified second strand to determine the location of the analyte in the biological sample.

18. The method of claim 1, wherein the biological sample comprises a formalin-fixed, paraffin-embedded (FFPE) tissue sample; a fresh tissue sample; or a frozen tissue sample.

19. The method of claim 1, wherein the second strand synthesis primer comprises a universal sequence.

20. The method of claim 1, wherein the second strand synthesis primer comprises a random sequence.

\* \* \* \* \*